United States Patent
Bittmann et al.

[11] Patent Number: 5,396,898
[45] Date of Patent: Mar. 14, 1995

[54] METHOD OF COMMINUTING SOFT TISSUE AS WELL AS MEANS OF PERFORMING THE METHOD

[75] Inventors: Peter Bittmann, Zürich; Daniel Nadler, Aadorf; Werner Müller-Glauser, Wiesendangen, all of Switzerland

[73] Assignee: Sulzer Medizinaltechnik AG, Winterthur, Switzerland

[21] Appl. No.: 123,462

[22] Filed: Sep. 17, 1993

[30] Foreign Application Priority Data

Oct. 2, 1992 [EP] European Pat. Off. ............ 92810742

[51] Int. Cl.$^6$ ............................................. A61B 10/00
[52] U.S. Cl. ................................... 128/749; 241/277
[58] Field of Search ................. 128/749, 751; 241/277

[56] References Cited
U.S. PATENT DOCUMENTS
4,028,190  6/1977  McAleer ............................. 435/287

FOREIGN PATENT DOCUMENTS
0219754  4/1987  European Pat. Off. .
1270511  7/1961  France .
1212248  3/1966  Germany .

Primary Examiner—Max Hindenburg
Attorney, Agent, or Firm—Townsend and Townsend Khourie and Crew

[57] ABSTRACT

The method of comminution of soft tissue (4) from animal or human bodies is performed by a mechanism (10) which exhibits a supply vessel (1), cutter member (2) and collector (3) and forms a closure impermeable to germs against the environment The tissue is removed from the body in a sterile environment, and filled into the supply vessel of the opened mechanism. After the supply vessel has been assembled together with the clutter member and the collector into a mechanism ready for operation, by the employment of pressure-exerting means, preferably compressed gas (11'), the tissue is delivered from the supply vessel into the collector, the tissue being comminuted at the same time by the cutter member.

17 Claims, 3 Drawing Sheets

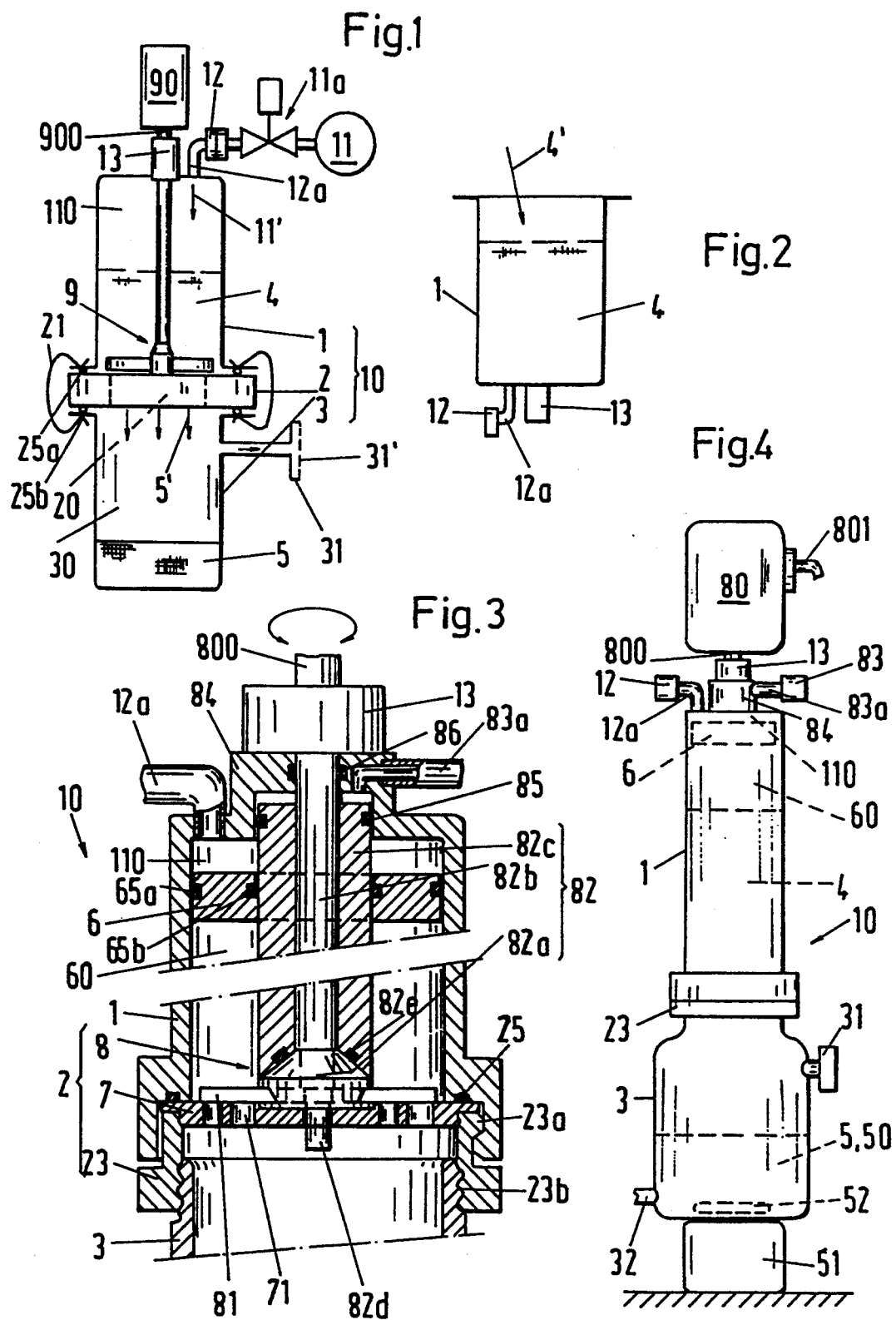

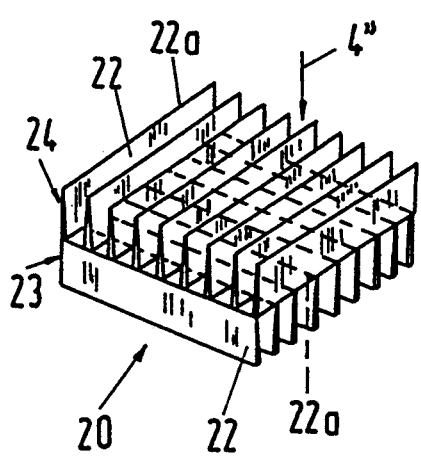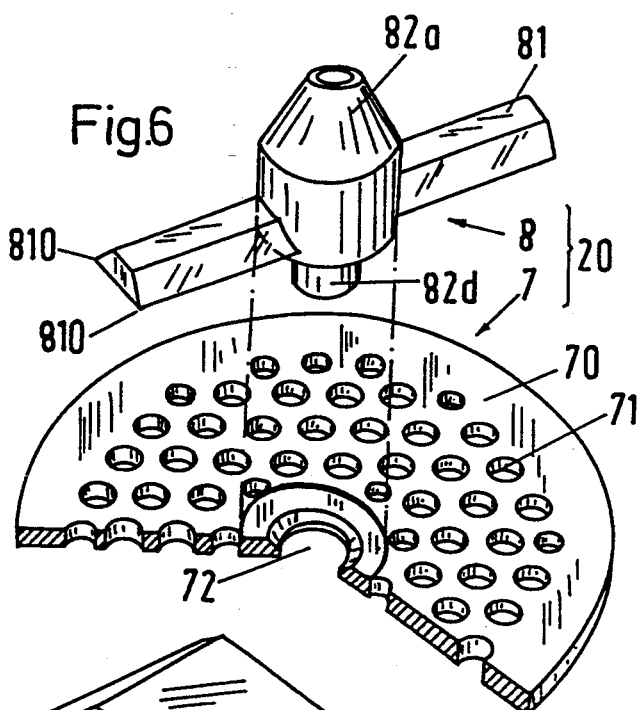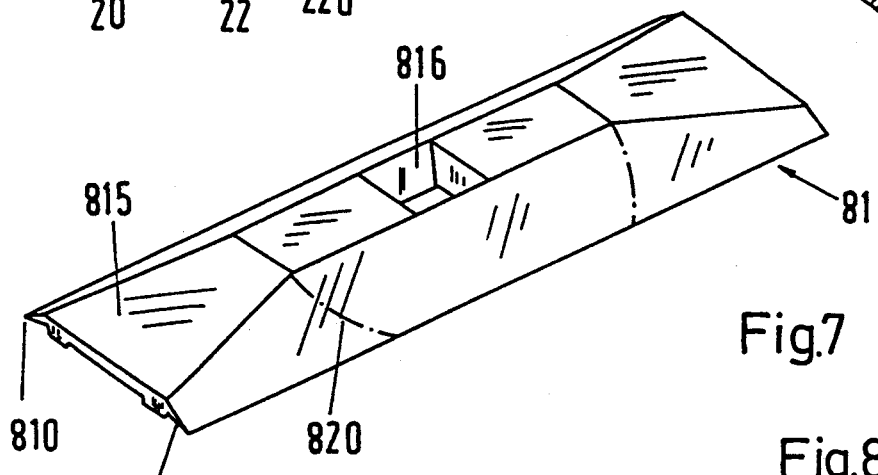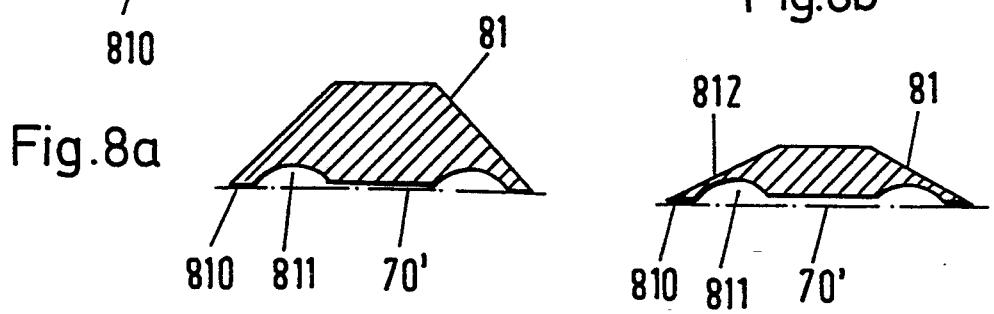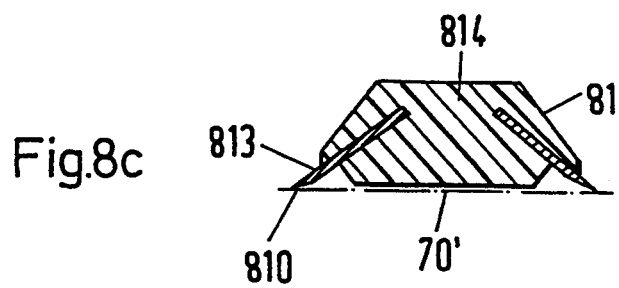

METHOD OF COMMINUTING SOFT TISSUE AS WELL AS MEANS OF PERFORMING THE METHOD

BACKGROUND OF THE INVENTION

The invention is concerned with a method of comminuting soft tissue from animal or human bodies as well as means of performing the method.

In the implantation of blood vessel prostheses for the replacement of arteries, for example, the practice is known of employing hybrid protheses. A vessel prosthesis of that kind consists of a hoselike porous plastics wall the inner surface of which is charged with endothelial cells belonging to the body. The cells may be obtained from fatty tissue from the patient, which contains microvascular endothelial cells (see B. E. Jarell et al.: "*Use of an endothelial monolayer on a vascular graft prior to implantation*", Ann. Surg 1986;203:671–678). The preparation of the hybrid prosthesis i.e., the obtaining of the cells as well as the coating of the plastics tube, must be carried out during the operation during which the replacement of the vessel is being effected; at most one hour is available for the preparation.

The surgeon removes the fatty tissue in pieces which weigh about 20–50 g. The pieces of tissue are then comminuted so that particles of tissue weighing about 0.03–0.1 g arise. By means of an enzymatic digestion in which the connecting tissue is partially broken down, the cells may be set free; they must still be separated from the fatty portion subsequently in a further step of the preparation.

The comminution of the pieces of tissue must be done gently by careful cutting in which as many cells as possible remain uninjured. In the known method comminution of the coarse pieces of tissue into small particles of tissue is carried out by elaborate handwork by means of a scalpel. This activity is made additionally difficult since sterility is necessary.

SUMMARY OF THE INVENTION

It is an objective of the invention to create a method by which rapid and gentle comminution of tissue from soft human or animal parts—while maintaining sterile conditions—may be carried out.

The present invention employs means of exerting pressure to effect the desired tissue comminution which preferably consist of a compressed gas by which with simultaneous utilization of gravity the tissue is driven through a cutter member. The tissue can also be delivered by means of a threaded spindle and a piston. Further possibilities consist in employing a liquid instead of gas for the force-transmitting medium, in which case the separation between the tissue and the liquid may be produced by means of a piston or a bellows.

The method in accordance with the invention which was originally developed for the comminution of fatty tissue may also be employed for other soft non-osseous tissue. The comminution of liver tissue may be named as an example. A method is known for washing out the blood, in which by means of pig's liver cells released and transferred to a substrate, blood from patients with inadequate functioning of the liver is detoxicated.

BRIEF DESCRIPTION OF THE DRAWINGS

FIG. 1 is a diagrammatic representation of a simple embodiment of the equipment constructed in accordance with the invention;

FIG. 2 shows a supply vessel removed from the equipment of FIG. 1;

FIG. 3 is a longitudinal section through a second embodiment of the comminuting mechanism in accordance with the invention, which exhibits a mincing machine-like cutter member;

FIG. 4 is an elevation of the embodiment shown in FIG. 3;

FIG. 5 is a cutter member for the embodiment of FIG. 1;

FIG. 6 shows parts of a mincing machine-like cutter member;

FIG. 7 shows a knife for a mincing machine-like cutter member;

FIGS. 8a to 8c are cross-sections through knives for mincing machine-like cutter members.

DETAILED DESCRIPTION OF THE PREFERRED EMBODIMENTS

Figure 9A:
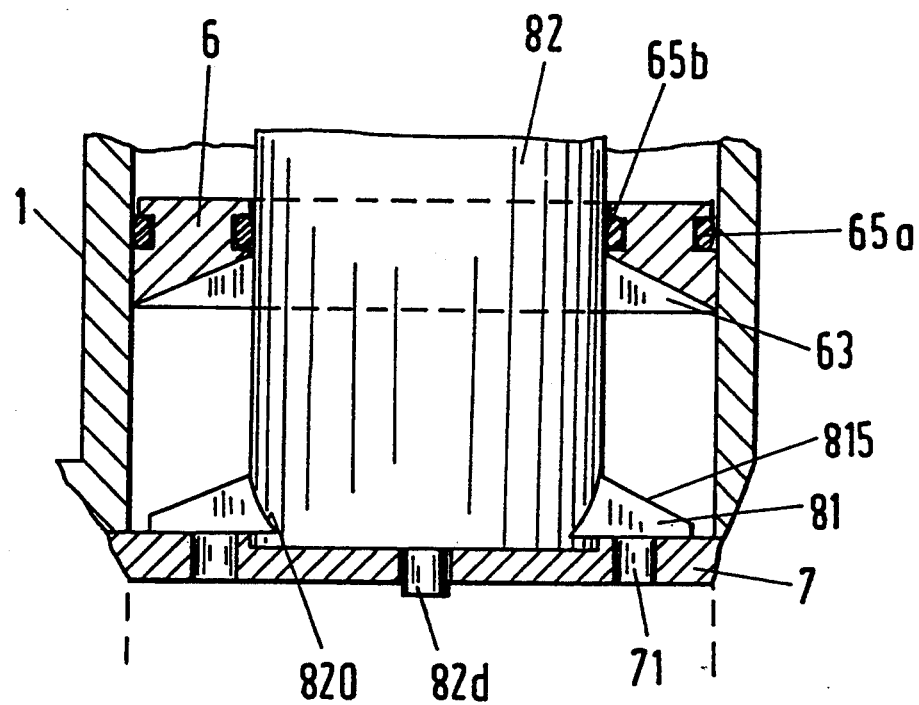
FIGS. 9a to 9b show a special embodiment of the mincing machine-like cutter member.
Figure 9B:
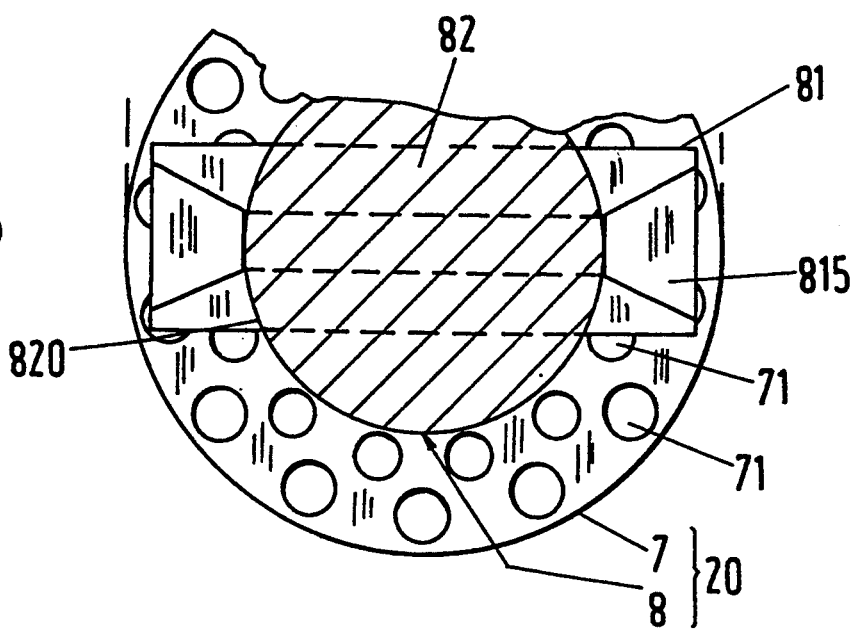

The equipment as in FIG. 1 consists in accordance with the invention of the mechanism 10 which is assembled from the supply vessel 1, the cutter member 2 and the collector 3 and also the source 11 of compressed gas. The supply vessel 1 may be removed from the equipment so that—see FIG. 2—the tissue 4 which is to be dealt with may be put into this vessel 1 (arrow 4'). For the cutter member 2 a means 20 of cutting is provided as shown in an oblique view in FIG. 5. A second embodiment of a possible cutting means 20 is represented in FIG. 6 as an exploded drawing; similarities exist with the cutting means of a mincing machine. In the case of the mechanism 10 of FIGS. 3 and 4 such a cutter member 2 like a mincing machine is provided. In the equipment when ready for operation the vessel 1 containing the tissue 4 is arranged above the cutter member 2 so that because of gravity the tissue rests upon the cutting means 20.

By means of clamps 21 and sealing rings 25a, 25b the mechanism 10 of FIG. 1 may be assembled from the three parts 1, 2 and 3 into one unit which forms for the tissue 4 which is to be treated and the comminuted tissue 5 a jacket impermeable to germs. In the case of the mechanism 10 in FIG. 3 the corresponding connection is produced by an intermediate ring 23 which is part of the cutter member 2 and is able to be connected to the supply vessel 1 via a bayonet joint 23a and to the collector 3 via a thread 23b. To seal the joint between the vessel 1 and the cutter member 2 a sealing ring 25 is provided. Obviously other possibilities of connection are also conceivable.

Thanks to its softness the tissue 4 forms in the supply vessel 1 of the assembled mechanism 10 a gas-tight closure between a gas space 110 and the cutting means 20. Compressed gas 11' is fed from the source 11 of compressed gas via the adjustable throttling member 11a and the detachable coupling point 12 to this gas space 110; the tissue 4 is thereby pressed through the cutter means 20 and at the same time comminuted, and delivered into the collector 3 (arrow 5'). In order that an overpressure shall not arise in the air space 30 in the said collector through the feed of comminuted tissue 5, a pressure-equalizing air release element 31 with a fine-pored outlet zone 31'—consisting, for example, of a sterile filter—is provided on the collector 3. The compressed gas 11' must be sterile and free from other impurities. In the supply vessel 1 a stirrer 9 turning slowly may serve to prevent gas breaking through from the gas space 110 into the air space 30 below the cutter member 2—at least as long as the amount of tissue 4 is adequate for doing that. The stirrer 9 may be connected via a coupling point 13 to the driving shaft 90a of a motor 90. The coupling point 13 must be made detachable like the coupling point 12, in order that the supply vessel 1 may be removed from the mechanism 10 and held so that the opening faces upwards (FIG. 2) for filling with tissue 4.

In order that no overpressure shall build up in the collector 3 to impede the cutting process, instead of the fine-pored outlet zone 31' of the air release element 31 there may also be provided, for example, an easily expandable rubber balloon. It is also conceivable to make the collector 3 in such a way that it can receive a variable volume, in which case it must be possible to bring about an enlargement in volume by a slight rise in pressure.

In the supply vessel 1 a piston 6 is advantageously provided (FIG. 3), which forms a movable but gas-tight closure (seals 65a, 65b) between the gas space 110 and an air space 60 in contact with the tissue 4 (see also FIG. 4). The sterility of the compressed gas 11' is thus no longer necessary and the risk of a breakthrough of gas between the gas space 110 and the air space 30 also no longer exists. It is also conceivable to provide instead of the piston a bellows-like separating device between the gas space 110 and the air space 60.

The cutting means represented in FIG. 5 consists of cutter blades 22 with cutting edges 22a which form a double grating of two grids 23 and 24 aligned at right angles across one another. The direction of conveyance of the tissue fed to the cutter member is indicated by the arrow 4''. The angle between the directions of the pair of grids may also differ from 90°.

The cutting means 20 of the cutter member, which is like a mincing machine as may be seen in FIG. 6, is composed of a perforated plate 7 and a movable component 8 with cutter elements 81 like knives. The cutting edges 810 of these knives 81 are movable over the plate 7 on the side 70 for entry of the tissue. The surface 70 is made plane and very smooth and the holes 71 exhibit inlet openings with sharp edges. The tissue is comminuted by the tissue while being pressed into the holes 71 becoming sheared between the knife edges 810 and the edges of the holes. The diameter of the hole may lie between 1 and 6 mm; preferably it lies in the range between 2 and 4 mm.

In the case of the embodiment described with the aid of FIGS. 3, 4 and 6 the supply vessel 1 is cylindrical and the movable component 8 is made as a turnable element. The cutter elements 81 are radial knifelike blades on a cylindrical shaft 82 the centerline of which coincides at least approximately with that of the supply vessel 1; the shaft 82 is connected via a detachable coupling point 13 to a driving shaft 800 of a motor 80 (power feed via the lead 801). The shaft 82 consists in accordance with FIG. 3 of a knife holder 82a, central rod 82b, jacket tube 82c, journal 82d for which a central bore 72 (see FIG. 6) is provided in the plate 7, and further a sealing ring 82e. The piston 6 made in the form of a ring encloses the shaft 82 tightly. The upper part of the shaft 82 is also made as a piston (sealing ring 85) which projects into the cylindrical housing 84. The passage of the rod 82b through the wall of the cylindrical housing 84 is sealed by a sealing ring 86.

By a second source (not shown) of compressed gas, for which a detachable coupling point 83 (FIG. 4) and a pipe 83a are provided, the knives 81 may be pressed pneumatically via the shaft 82 against the perforated plate 7. The pneumatically generated pressure may in the case of the same pressure of the compressed gas be cancelled by means of structural measures, that is by an increase in the area acted upon by pressure and a corresponding enlargement of the cylindrical housing 84. It has been established by experiment that the pressure must amount—referred to the total length of the cutting edges 810—to at least about 2,500 N/m.

In order that as much as possible of the tissue to be dealt with can arrive in the working range of the cutting means 20 the knife 81 must be made flat. It must consist of material stiff in bending which allows the pressures needed to be made to act against the surface 70 uniformly over the whole length of the cutting edge 810. For the sake of simplicity the knife 81 exhibits constant cross-section as is the case in FIG. 6. But it is also possible to give the knife 81 a cross-section which tapers in radially outwards. A knife 81 of that kind is shown in FIG. 7. On the upper face of the knife between the surface of the shaft which is indicated as the dash-dot curve 820, and the outer edges of the knife, areas 815 running obliquely are provided. (The square opening 816 in the center of the knife is provided for the engagement of a square via which the torque from the shaft 82 is transmitted to the knife 81.)

With the aid of cross-sections in FIGS. 8a to 8c further examples of the cutting element 81 are shown. The position of the surface 70 of the plate is specified by the dash-dot line 70'. In parallel with the cutting edge 810 grooves 811 are provided which facilitate grinding of the edge. In the case of the flat knife 81 of FIG. 8b a thin place 812 behind the cutting edge 810 results through the groove 811, by which in the case of a suitable choice of material a springy resilience of the cutting edge may be generated. FIG. 8c shows a knife 81 in which cutter blades 813 are case into a foundation 814 of plastics.

The cutting member represented in FIGS. 9a, b exhibits a knife 81 of the kind shown in FIG. 7. In the case of the piston 6 an underside 63 is provided which is made conical to correspond. With this formation a smaller residue of tissue arises which cannot be comminuted, than in the case of the mechanism in accordance with FIG. 3 where the underside of the piston runs in parallel with the surface 70 of the plate and the knife 81 exhibits constant cross-section. The choice of a large diameter of the shaft 82, because of which the perforated annular part of the plate 7 comes out considerably smaller than in the case of the dimensions in accordance with FIG. 6, contributes to the non-comminutable part of the tissue becoming further reduced.

The annular pistons 6 in FIGS. 3 and 9a exhibit in each case an inner sealing ring 65b and an outer 65a. In order to obtain better sealing between the spaces 110 and 60 (FIG. 3) as well as better slidability of the piston 6, two sealing rings may be provided in each case.

In comminuting fatty tissue by means of a cutter member 2 like a mincing machine with rotating cutting elements 81 problems have arisen with collagen fibers. These fibers which remain partially incompletely cut up impede the conveyance of the comminuted tissue 5 through the perforated plate 7 and impair the cutting process. Fibers also wind themselves partially around shaft 82. By the cutting elements 81 being pressed against the perforated plate 7 with a relatively heavy force and by the direction of rotation being reversed periodically—after turning each time through about 180°—the impairment of the method in accordance with the invention may be eliminated. In order to make the reversing motion possible, the cutting elements 81 are made with two cutting edges 810 as shown in FIGS. 6 to 8c. Obviously a driving motor 80 also has to be provided (FIG. 4) by which the advantageous to-and-fro motion of the cutting elements 81 may be executed.

As mentioned initially, the mechanical comminution of the tissue 4 may be followed by an enzymatic digestion in which the comminuted tissue 5 becomes disintegrated and individual cells become released. The collector 3 is advantageously used for the performance of this digestion (see FIG. 4): in the collector 3 the comminuted tissue 5 is brought into contact with a solution 50 of an enzyme—collagenase, for example. In that case a magnetic stirrer 52 with a drive 51 sees to thorough mixing of the enzyme solution and tissue. After digestion has been effected the mixture 5, 50 may be removed from the collector 3 via an outlet 32 for further steps of the method (separation of the cells from fat and enzyme).

We claim:

1. A method for comminuting soft tissue comprising the steps of providing a supply vessel, a collector and a cutter; placing the soft tissue into the supply vessel while maintaining the tissue in a sterile environment; assembling the supply vessel, the cutter and the collector into a comminuting mechanism ready for operation; closing the supply vessel, the collector and the cutter to maintain the tissue placed in the supply vessel sterile; applying pressure to the tissue in the supply vessel and activating the cutter to comminute the tissue and force the tissue from the supply vessel into the collector; and collecting comminuted tissue in the collector.

2. A method according to claim 1 including the step of contacting the comminuted tissue in the collector with an enzyme solution.

3. Apparatus for comminuting soft tissue comprising:
   a supply vessel defining a tissue holding chamber;
   a collector for receiving comminuted tissue;
   a cutting member;
   means for sealingly connecting the vessel, the collector and the cutting member;
   a source of a compressed gas;
   a fluid coupling detachably fluidly connecting the source and the chamber;
   a gas pressure reducer disposed between the source and the chamber for regulating the pressure of gas entering the chamber; and
   a gas pressure relief element fluidly coupled with an interior of the collector.

4. Apparatus according to claim 3 wherein the supply vessel defines a cylindrical supply chamber, and including a piston axially movably disposed within the chamber and defining a tissue subspace on one side of the piston and a compressed gas subspace on another side of the piston.

5. Apparatus according to claim 3 wherein the cutting member is defined by first and second sets of transversely arranged cutter blades which form a rectilinear grid of blades.

6. Apparatus according to claim 5 including a stirrer disposed in the chamber of the supply vessel, a drive motor for the stirrer, and a coupling detachably connecting the stirrer to the drive motor.

7. Apparatus according to claim 3 wherein the cutting member comprises a perforated plate disposed at an interface between the supply vessel and the collector and having a first side facing the chamber of the supply vessel, and a cutting element in the chamber having cutting edges which are movable over the first side of the plate.

8. Apparatus according to claim 7 wherein the chamber has a cylindrical configuration, and including a shaft disposed in the chamber and rotatable about an axis at least approximately concentric with an axis of the chamber, a drive motor, and a coupling detachably connecting the shaft to the motor, and wherein the cutting elements comprise knife-like, generally radially oriented blades which project from the shaft.

9. Apparatus according to claim 8 wherein the drive motor is adapted to move the cutting elements towards and away from the perforated plate.

10. Apparatus according to claim 8 wherein perforations in the perforated plate are distributed over an annular zone of the perforated plate, a core section of the perforated plate radially inward from and contiguous with an inner diameter of the annular zone being free of perforations, and wherein a diameter of the core section is at least approximately equal to a diameter of the shaft.

11. Apparatus according to claim 7 including means biasing the cutting elements against the perforated plate.

12. Apparatus according to claim 11 wherein the biasing means comprises a further source of a compressed gas and means for generating the biasing force with the compressed gas from the further source.

13. Apparatus according to claim 12 including a shaft disposed in the chamber, and wherein the biasing force is exerted by the shaft.

14. Apparatus according to claim 7 wherein the perforated plate has a multiplicity of holes having a diameter in the range of between 1 mm and 6 mm.

15. Apparatus according to claim 14 wherein the holes have a diameter of between 2 mm and 4 mm.

16. A method of charging an inside of a blood vessel prosthesis with endothelial cells from fatty human or animal tissue comprising the steps of removing the tissue from a live body; providing a supply vessel, a collector and a cutter; placing the tissue into the supply vessel while maintaining the tissue in a sterile environment; assembling the supply vessel, the cutter and the collector into a comminuting mechanism ready for operation; closing the supply vessel, the collector and the cutter to maintain the tissue placed in the supply vessel sterile; applying pressure to the tissue in the supply vessel and activating the cutter to comminute the tissue and force the tissue from the supply vessel into the collector; and collecting comminuted tissue in the collector.

17. A method of cleansing a patient's blood having a malfunctioning liver comprising the steps of obtaining a live pig's liver tissue; providing a supply vessel, a collector and a cutter; placing the tissue into the supply vessel while maintaining the tissue in a sterile environment; assembling the supply vessel, the cutter and the collector into a comminuting mechanism ready for operation; closing the supply vessel, the collector and the cutter to maintain the tissue placed in the supply vessel sterile; applying pressure to the tissue in the supply vessel and activating the cutter to comminute the tissue and force the tissue from the supply vessel into the collector; and collecting comminuted tissue in the collector.

* * * * *